United States Patent [19]

Mengel et al.

[11] Patent Number: 4,509,972
[45] Date of Patent: Apr. 9, 1985

[54] N-PTERIDINYL-UREAS

[75] Inventors: Rudolf Mengel; Ludwig Schröder, both of Ingelheim; Werner Stransky, Gau-Algesheim; Gerbert Linden, Ingelheim; Gerhart Schneider, Mühltal; Sigmund Lust, Darmstadt, all of Fed. Rep. of Germany

[73] Assignee: Celamerck GmbH & Co. KG, Ingelheim am Rhein, Fed. Rep. of Germany

[21] Appl. No.: 479,708

[22] Filed: Mar. 28, 1983

[30] Foreign Application Priority Data

Apr. 10, 1982 [DE] Fed. Rep. of Germany ....... 3213507
May 21, 1982 [DE] Fed. Rep. of Germany ....... 3219145
Jul. 28, 1982 [DE] Fed. Rep. of Germany ....... 3228100

[51] Int. Cl.³ ............... A01N 43/90; C07D 475/04; C07D 475/08
[52] U.S. Cl. ............... 71/92; 544/258; 544/260
[58] Field of Search ............... 71/92; 544/258, 260

[56] References Cited

U.S. PATENT DOCUMENTS 4,333,760  6/1982  Zimmerman .......... 71/92
4,420,325 12/1983  Sauers .......... 71/92

Primary Examiner—Paul M. Coughlan, Jr.
Attorney, Agent, or Firm—Hammond & Littell, Weissenberger & Dippert

[57] ABSTRACT

Compounds of the formula

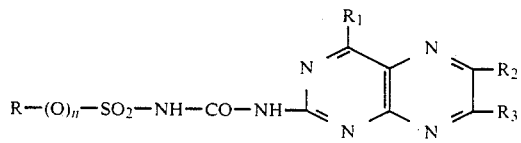

wherein R, $R_1$, $R_2$ and $R_3$ are substituents of diverse types, and salts thereof. The compounds as well as their salts are useful as herbicides.

9 Claims, No Drawings

N-PTERIDINYL-UREAS

OBJECTS OF THE INVENTION

It is an object of the invention to provide the novel compounds of formula I and their acid addition salts and a process for their preparation.

It is another object of the invention to provide novel herbicidal compositions and to a novel method of combatting weeds.

These and other objects and advantages of the invention will become obvious from the following detailed description.

THE INVENTION

The novel compounds of the invention are selected from the group consisting of N-pteridinyl-ureas of the formula

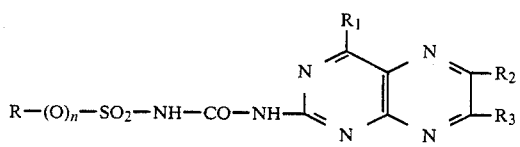

wherein R is selected from the group consisting of

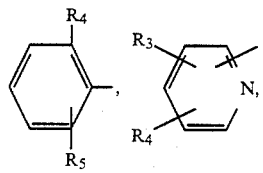

alkyl of 1 to 12 carbon atoms optionally interrupted by an oxygen atom and optionally halogenated, unsaturated hydrocarbon of 2 to 12 carbon atoms containing up to three double bonds, cycloaliphatic with 3 to 7 ring carbon atoms optionally unsaturated and optionally halogenated or alkyl substituted containing a total up to 12 carbon atoms, —$CH_2Q$, Q is selected from the group consisting of —CN, —$COOR_6$, 2,2-dichlorocyclopropyl and phenyl optionally substituted with at least one member of the group consisting of fluoro, chloro, bromo, alkyl, alkylthio or alkoxy of 1 to 6 carbon atoms, —CN and —$COOR_6$, n is one or zero, $R_1$ is selected from the group consisting of hydrogen, alkyl, alkoxy or alkylthio of 1 to 6 carbon atoms, halogen, —$NH_2$ and mono and di alkylamino of 1 to 6 alkyl carbon atoms, $R_2$ and $R_3$ are individually selected from the group consisting of hydrogen, and alkyl of 1 to 6 carbon atoms, $R_4$ is selected from the group consisting of halogen, alkoxy carbonyl of 2 to 7 carbon atoms, optionally halosubstituted alkyl and alkoxy of 1 to 6 carbon atoms, alkylthio of 1 to 6 carbon atoms, —CN, cycloalkyl of 3 to 7 ring carbon atoms optionally substituted with at least one member of the group consisting of 1 to 6 carbon atoms, —$NO_2$ alkyloxy, dialkylamino of 1 to 6 alkyl carbon atoms, —X—$SO_2R_7$,

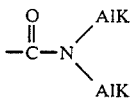

and

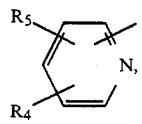

AlK is alkyl of 1 to 4 carbon atoms, $R_5$ is selected from the group consisting of hydrogen, halogen, alkoxycarbonyl of 2 to 7 carbon atoms, alkyl or alkoxy or alkylthio of 1 to 6 carbon atoms, —$CH_3$, —CN and cycloalkyl of 3 to 7 ring carbon atoms optionally substituted with at least one member of the group consisting of —$NO_2$, alkyl of 1 to 6 carbon atoms and dialkylamino of 1 to 6 alkyl carbon atoms, $R_6$ is alkyl of 1 to 6 carbon atoms, $R_7$ is alkyl of 1 to 6 carbon atoms optionally substituted with alkoxy of 1 to 6 carbon atoms or 1 to 3 halogens, X is selected from the group consisting of —O—, —NH—, —N—AlK and —C—S— and their acid addition salts.

Among the preferred group are lower alkyl, lower alkoxy and lower alkylthio of 1 to 4 carbon atoms such as methyl, ethyl, n-propyl, isopropyl, n-butyl, isobutyl, sec.-butyl and tert.-butyl. The preferred alkyls are methyl and ethyl. If R is

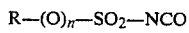

n is preferably zero. $R_2$ and $R_3$ are preferably methyl or hydrogen and $R_1$ is preferably methyl, methoxy, chlorine, amino, methylamino or dimethylamino. Halogen includes bromine, iodine, chlorine and fluorine, preferably fluorine, chlorine or bromine and most preferably chlorine.

The process of the invention for the preparation of a compound of formula I comprises reacting a sulfonyl isocyanate of the formula $$R-(O)_n-SO_2-NCO \qquad IV$$

wherein n and R have the above definition with an amine of the formula

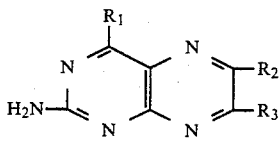

wherein $R_1$, $R_2$ and $R_3$ have the above definition.

The reaction is preferably performed in an aprotic solvent such as methylene chloride or acetonitrile, and the amino compound is added gradually to the isocyanate with stirring and, if desired, with cooling. The reaction is completed at room temperature or at elevated temperatures up to the boiling point of the reaction mixture, the resulting product is isolated and, if desired, purified by usual methods. It is advantageous to react the compounds in the absence of water.

The sulfonyl isocyanates of formula IV used as starting material can be obtained by conventional processes, such as that described in J. Org. Chem. 39, 1597, ff. (1974). The phenoxysulfonyl isocyanates of formula IV can be prepared according to the procedure of Lohaus, Chem. Ber. 105, 2791-2799 (1972). In general, it is not necessary to purify these compounds for further reaction. The phenyl- or pyridylsulfonyl isocyanates of formula IV are known or can be prepared analogously to known compounds of this type, e.g. according to German patent 817,602, U.S. Pat. No. 3,379,758, European Pat. No. 21 641 or H. Ulrich, Chem. Ber. 65, 369 (1965).

The pteridines of formula V used as starting materials can be prepared according to known procedures such as Pfeiderer et al., Chem. Ber., Vol. 93,2015 (1960) and Vol. 103, p. 722 (1970).

Another process for the preparation of a compound of formula I comprises reacting a carbamate of the formula

R—(O)$_n$—SO$_2$—NH—CO—OC$_6$H$_5$     VI wherein n and R have the above definitions with an amine of formula V.

The carbamates of formula VI can be obtained by reacting an amide of the formula

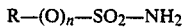
R—(O)$_n$—SO$_2$—NH$_2$     VII and diphenyl carbonate in the presence of a base in a manner known per se. Also the compounds of formula VII can be prepared in a known manner.

If desired, the compounds of formula I resulting from the said processes can be reacted with suitable alkali metal or alkaline earth metal compounds or with organic bases to form the corresponding salts. This is preferably carried out by reacting the compound of formula I with the calculated amount of the base.

The novel herbicidal compositions of the invention are comprised of a herbicidally effective amount of at least one compound of formula I and its salts and an inert carrier. The compositions may be in the form of powders, wettable powders, solutions, emulsions, etc. prepared in the usual manner.

The compositions of the invention are distinguished by their strong herbicidal activity and they can be applied both pre-emergence and post-emergence against numerous monocotyledonous and dicotyledonous weeds, e.g. wild mustard, catchweed, bedstraw, amaranth, goose-foot, camomile, blackgrass, barnyardgrass, yellow nutsedge, purple nutsedge, wild oats. Due to their selectivity, the compositions may be used for combatting weeds in a variety of crops, such as in wheat, corn, rice, barley, potatoes, tomatoes, sunflowers, peas, beans, beets, turnips and cotton.

For use as herbicides, the compounds of formula I and their salts are processed in known manner with conventional auxiliaries and/or carriers, e.g. to form emulsion concentrates or wettable powders wherein the content of active ingredient is between 10 and 95% by weight, and which can be adjusted to the desired concentration of active substance by adding water. However, preparations may also be made for use in undiluted form, such as dusting powders or granules. In this case, the content of active substances is between 0.01 and 10% by weight, preferably 0.1 and 3% by weight.

The novel method of the invention for combatting weeds comprises contacting weeds with a herbicidal amount of at least one compound of formula I and their salts.

Examples of suitable acids for the acid addition salts of the compounds of formula I are inorganic acids such as hydrochloric acid, hydrobromic acid, sulfuric acid, nitric acid and phosphoric acid and organic acids such as acetic acid, propionic acid, citric acid, maleic acid, tartaric acid, etc.

In the following examples there are described several preferred embodiments to illustrate the invention. However, it is to be understood that the invention is not intended to be limited to the specific embodiments.

EXAMPLE 1

N-(4-methoxypteridin-2-yl)-N'-(2-chlorophenylsulfonyl)-urea

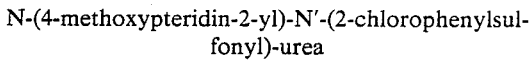

1.5 g (0.0069 mol) of 2-amino-4-methoxypteridine and two drops of triethylamine were added to a mixture of 1.77 g (0.01 mol) of 2-chlorophenylsulfonyl isocyanate in 20 ml of acetonitrile and the mixture was refluxed for 30 minutes, cooled and mixed with diisopropyl ether. After standing for 10 minutes, the mixture was vacuum filtered to obtain 2.25 g (87% of theory) of N-(4-methoxypteridin-2-yl)-N'-(2-chlorophenylsulfonyl)-urea melting at 212° C.

EXAMPLE 2

N-(4-dimethylamino-6,7-dimethylpteridin-2-yl)-N'-(2-carbomethoxyphenylsulfonyl)-urea

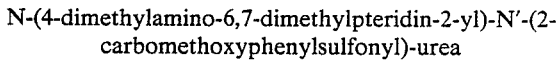

A mixture of 1 g of 2-amino-4-dimethylamino-6,7-dimethylpteridine and 1.3 g of 2-carbomethoxyphenylsulfonyl isocyanate was stirred in 10 ml of acetonitrile for 30 minutes at room temperature and then the mixture was heated to reflux for 3 to 4 minutes. After cooling diisopropyl ether was added thereto and the mixture was vacuum filtered to obtain 1.7 g (81% of theory) of N-(4-dimethylamino-6,7-dimethylpteridin-2-yl)-N'-(2-carbomethoxyphenylsulfonyl)-urea melting at 196° C.

EXAMPLE 3

N-(4-methoxy-6,7-dimethylpteridin-2yl)-N'-(2-carbomethoxyphenylsulfonyl)-urea.

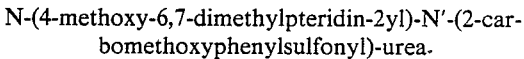

After addition of 2 drops of triethylamine, a mixture of 1.02 g (0.005 mol) of 2-amino-4-methoxy-6,7-dimethylpteridine and 1.92 g (0.008 mol) of carbomethoxyphenylsulfonyl isocyanate in 20 ml acetonitrile was refluxed for 45 minutes. After cooling, diisopropyl ether was added thereto and after 30 minutes, the mixture was vacuum filtered. The sparringly soluble product was dissolved in dimethylformamide and precipitated with ethanol to obtain 1.95 g (85% of theory) of N-(4-methoxy-6,7-dimethylpteridin-y-2-yl)-N'-(2-carbomethoxyphenylsulfonyl)-urea melting at 181° C.

EXAMPLE 4

N-(4-methoxypteridin-2-yl)-N'-(2-fluorophenoxysulfonyl)-urea

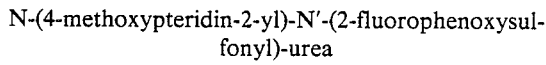

0.88 g (0.005 mol) of 2-amino-4-methoxypteridine were suspended in 40 ml of methylene chloride and 1.2 g (0.0055 mol) of 2-fluorophenoxysulfonyl isocyanate were added thereto rapidly to obtain a clear solution. The solution was heated to reflux for a short time, thereafter stirred for 10 minutes and then was concentrated by evaporation to dryness. The residue was treated with diisopropyl ether and a little acetone and the mixture was vacuum filtered. The product was dried to obtain 1.95 of N-(4-methoxypteridin-2-yl)-N'-(2-fluorophenoxysulfonyl)-urea in the form of light yellow crystals melting at 135° C.

EXAMPLE 5

N-(4-methoxypteridine-2-yl)-N'-(2-trifluoromethylphenylsulfonyl)-urea 0.88 g (0.005 mol) of 2-amino-4-methoxypteridine and 1.30 g (0.0052 mol) of 2-trifluoromethylphenylsulfonyl isocyanate were reacted in 40 ml of methylene chloride according to Example 4 to obtain 2.0 g (94% of theory) of N-4-methoxypteridin-2-yl)-N'-(2-trifluoromethylphenylsulfonyl)-urea in the form of light yellow crystals melting at 187° C.

EXAMPLE 6

N-(4-dimethylaminopteridine-2yl)-N'-(2-chlorophenylsulfonyl)-urea 1.5 g (0.0070 mol) of 2-chlorophenylsulfonyl isocyanate were added to a suspension of 1.3 g (0.0068 mol) of 2-amino-4-dimethylaminopteridine in 40 ml of acetonitrile and the mixture was stirred at reflux for 4 hours. The mixture was vacuum filtered and the filtrate was concentrated by evaporation. The residue was treated with acetone to obtain 2.05 g (74% of theory) of N-(4-dimethylaminopteridine-2-yl)-N'-(2-chlorophenylsulfonyl)-urea in the form of light yellow crystals melting at 232° C.

EXAMPLE 7

N-(4-dimethylaminopteridin-2-yl)-N'-(2-methoxycarbonylphenylsulfonyl)-urea

A mixture of 1.3 g (0.0068 mol) of 2-amino-4-dimethylaminopteridine and 1.7 g of 2-methoxycarbonylphenylsulfonyl isocyanate in 40 ml of acetonitrile was refluxed for 4 hours and the hot mixture was vacuum filtered to obtain 2.5 g (85% of theory) of N-(4-dimethylaminopteridin-2-yl)-N'-(2-methoxycarbonylphenylsulfonyl)-urea in the form of brownish crystals melting at 219° C.

EXAMPLE 8

N-(4-methoxypteridin-2-yl)-N'-(2-carbomethoxyphenylsulfonyl)-urea 1.68 g (0.005 mol) of N-(2-carbomethoxyphenylsulfonyl)-phenylcarbamate (obtained from the corresponding sulfonamide and diphenylcarbonate) were refluxed in 30 ml of absolute dioxane for 8 hours. After evaporation to dryness, the residue was treated twice with an aqueous solution of sodium bicarbonate and several times with water. Water and a little of acetone were added and crystallization was initiated by scratching to obtain 1.85 g (80% of theory) of N-(4-methoxy pteridin-2-yl)-N'-(2-carbomethoxyphenylsulfonyl)-urea in the form of brownish crystals which after recrystallization from ethanol-dimethylformamide melting at 188° C.

EXAMPLE 9

N-(4-methoxypteridin-2-yl)-N'-(2,2,2-trichloroethoxysulfonyl)-urea

To a suspension of 0.88 g (0.005 mol) of 2-amino-4-methoxypteridine in 40 ml of absolute methylene chloride were added with stirring to 1.35 g (0.053 mol) of 2,2,2-trichloroethoxysulfonyl isocyanate. After about 10 minutes, a clear solution had formed and it was heated to reflux. After 10 minutes, the mixture was evaporated to dryness and the residue was treated with diisopropyl ether and a little acetone. The mixture was vacuum filtered and the product was dried to obtain 2.05 g (95% of theory) of N-(4-methoxypteridin-2-yl)-N'-(2,2,2-trichloroethoxysulfonyl)-urea in the form of yellow crystals melting at 93° C. (decomp.).

The compounds of formula I listed in the following table were obtained analogously to the process of the above examples to obtain compounds of the formula

TABLE I $R_4$-phenyl-$(O)_n$-$SO_2$-NH-CO-NH-pteridinyl with $R_1, R_2, R_3$ substituents

| No. | n | $R_4$ | $R_5$ | $R_1$ | $R_2$ | $R_3$ | m.p. [°C.] |
|---|---|---|---|---|---|---|---|
| 10 | 0 | $CF_3$ | H | $OCH_3$ | H | H | 187 |
| 11 | 0 | $OCHF_2$ | H | $OCH_3$ | H | H | |
| 12 | 0 | F | 4-F | $CH_3$ | H | H | |
| 13 | 0 | Cl | 4-$CH_3$ | F | H | H | |
| 14 | 0 | $CH_3$ | 4-Cl | Cl | $CH_3$ | $CH_3$ | |
| 15 | 0 | $OC_2H_5$ | H | Cl | H | H | |
| 16 | 0 | $COOC_2H_5$ | H | $OCH_3$ | H | H | |
| 17 | 0 | Br | H | $NH_2$ | H | H | |
| 18 | 0 | Cl | 4-Cl | $NHCH_3$ | H | H | |
| 19 | 0 | $OCHF_3$ | H | $N(CH_3)_2$ | H | H | |
| 20 | 1 | $CH_3$ | H | $OCH_3$ | $CH_3$ | $CH_3$ | |
| 21 | 1 | Cl | H | $NHCH_3$ | H | H | |
| 22 | 1 | $OC_2H_5$ | H | Cl | H | H | |
| 23 | 1 | $COOCH_3$ | H | $OCH_3$ | H | H | 188 |
| 24 | 1 | $OCHF_2$ | H | $N(CH_3)_2$ | H | H | |
| 25 | 1 | Cl | H | Br | H | H | |
| 26 | 1 | Br | H | $CH_3$ | H | H | |
| 27 | 1 | $OCF_3$ | H | $OCH_3$ | H | H | |
| 28 | 1 | $SCH_3$ | 4-$CH_3$ | $OCH_3$ | H | H | |
| 29 | 1 | F | 5-$CH_3$ | $NHCH_3$ | H | H | |
| 30 | 0 | $CF_3$ | H | $N(CH_3)_2$ | H | H | 192 |
| 31 | 1 | $COOCH_3$ | H | $N(CH_3)_2$ | H | H | 153 |
| 32 | 1 | F | H | $OCH_3$ | H | H | 135 |
| 33 | 1 | $COOCH_3$ | H | $OCH_3$ | H | H | 153 |
| 34 | 0 | $COOCH_3$ | H | $N(CH_3)_2$ | H | H | 215 |
| 35 | 0 | $CF_3$ | H | $N(CH_3)_2$ | H | H | 187 |
| 36 | 0 | $CF_3$ | H | $OCH_3$ | H | H | 214 |
| 37 | 0 | $COOCH_3$ | H | $OCH_3$ | H | H | 188 |
| 38 | 0 | $CF_3$ | H | $NH_2$ | H | H | 275 |
| 39 | 0 | $COOCH_3$ | H | $NH_2$ | H | H | 225 |
| 40 | 0 | Cl | H | $NH_2$ | H | H | 270 |
| 41 | 0 | Cl | H | $N(C_2H_5)_2$ | H | H | 221 |
| 42 | 0 | $OCH_3$ | 5-Br | $N(CH_3)_2$ | H | H | 248 |
| 43 | 0 | Cl | H | $NH_2$ | $CH_3$ | $CH_3$ | 232 |
| 44 | 0 | Cl | H | $N(CH_3)_2$ | H/$CH_3$* | | 204 |
| 45 | 0 | $COOCH_3$ | H | $N(CH_3)_2$ | H/$CH_3$* | | 215 |
| 46 | 0 | $CON(CH_3)_2$ | H | $N(CH_3)_2$ | H | H | 193 |

*Product is a mixture wherein the methyl group is partly in 6-and partly in 7-position.

Using an analogous process to the above examples, the following compounds of the formula were prepared

TABLE II $CCl_3$-$CH_2$-O-$SO_2$-NH-CO-NH-pteridinyl with $R_1, R_2, R_3$ substituents

| No. | $R_1$ | $R_2$ | $R_3$ |
|---|---|---|---|
| 47 | $OCH_3$ | H | H |
| 48 | $OCH_3$ | H | H |
| 49 | $CH_3$ | H | H |
| 50 | F | H | H |
| 51 | Cl | $CH_3$ | $CH_3$ |
| 52 | Cl | H | H |
| 53 | $OCH_3$ | H | H |

TABLE II-continued

CCl₃—CH₂—O—SO₂—NH—CO—NH— [pyrimidine structure with R₁, R₂, R₃]

| No. | R₁ | R₂ | R₃ |
|---|---|---|---|
| 54 | NH₂ | H | H |
| 55 | NHCH₃ | H | H |
| 56 | N(CH₃)₂ | H | H |
| 57 | OCH₃ | CH₃ | CH₃ |
| 58 | NHCH₃ | H | H |
| 59 | Cl | H | H |
| 60 | OCH₃ | H | H |
| 61 | N(CH₃)₂ | H | H |
| 62 | Br | H | H |
| 63 | CH₃ | H | H |
| 64 | OCH₃ | H | H |
| 65 | OCH₃ | H | H |
| 66 | NHCH₃ | H | H |
| 67 | N(CH₃)₂ | H | H |
| 68 | N(CH₃)₂ | H | H |

Using a process of the above examples the compounds of the formula were prepared

TABLE III

R—SO₂—NH—CO—NH— [pyrimidine structure with R₁, R₂, R₃]

| No. | R₁ | R₂ | R₃ | R | m.p. [°C.] |
|---|---|---|---|---|---|
| 69 | OCH₃ | H | H | CH₃ | |
| 70 | OCH₃ | H | H | CH₂—[cyclopropyl]—Cl, Cl | |
| 71 | CH₃ | H | H | n-C₄H₉ | |
| 72 | F | H | H | t-C₄H₉ | |
| 73 | Cl | CH₃ | CH₃ | n-C₃H₇ | |
| 74 | Cl | H | H | n-C₄H₉ | |
| 75 | OCH₃ | H | H | i-C₃H₇ | |
| 76 | NH₂ | H | H | n-C₆H₁₃ | |
| 77 | NHCH₃ | H | H | n-C₃H₇ | |
| 78 | N(CH₃)₂ | H | H | n-C₁₂H₂₅ | |
| 79 | OCH₃ | CH₃ | CH₃ | C₂H₅ | |
| 80 | NHCH₃ | H | H | [cyclobutyl] | |
| 81 | Cl | H | H | [cyclopropyl] | |
| 82 | OCH₃ | H | H | CH₂=CH—CH₂ | |
| 83 | N(CH₃)₂ | H | H | CH₂=CH—CH₂ | |
| 84 | Br | H | H | [cyclopentenyl] | |
| 85 | CH₃ | H | H | [cyclohexyl] | |
| 86 | OCH₃ | H | H | i-C₃H₇ | |
| 87 | OCH₃ | H | H | CH₃—CH=CH—CH₂ | |
| 88 | NHCH₃ | H | H | n-C₆H₁₃ | |
| 89 | N(CH₃)₂ | H | H | n-C₃H₇ | |
| 90 | N(CH₃)₂ | H | H | i-C₄H₉ | |

Using the process of the above examples, the compounds of formula I indicated in Table IV were prepared

TABLE IV

| No. | n | R | R₁ | R₂ | R₃ | m.p. [°C.] |
|---|---|---|---|---|---|---|
| 91 | 1 | CCl₃—CH₂ | OCH₃ | H | H | 92 (decomp.) |
| 92 | 0 | [2-chloropyridin-3-yl] | N(CH₃)₂ | H | H | 207 |
| 93 | 0 | [2-chloropyridin-3-yl] | OCH₃ | H | H | 227 |
| 94 | 0 | [2-chloropyridin-3-yl] | NH₂ | H | H | 230 |
| 95 | 0 | n-C₃H₇ | N(CH₃)₂ | H | H | 178 |

Formulation Examples

A. A dusting powder was prepared by admixing 0.3% by weight of a compound of formula I, 98.7% by weight of talc and 1.0% by weight of methylcellulose.

B. A suspension powder was prepared containing 25% by weight of a compound of formula I, 55% by weight of kaolin, 10% by weight of colloidal silicic acid, 9% by weight of calcium lignin sulfonate and 1% by weight of sodium tetrapropylenebenzenesulfonate.

C. A suspension powder was prepared containing 95% by weight of a compound of formula I, 4% by weight of calcium lignin sulfonate and 1% by weight of sodium tetrapropylenebenzenesulfonate.

D. An emulsion concentrate was prepared containing 20% by weight of a compound of formula I and 70% by weight of a liquid solvent mixture of high-boiling aromatic hydrocarbons (Shellsol A), 6.5% by weight of Tensiofix AS (emulsifier) and 3.5% by weight of Tensiofix DS (emulsifier). Spray compositions were prepared from the concentrates according to Examples A and B by mixing with water to obtain spray compositions containing about 0.001, preferably 0.01 to 0.5 by weight of active ingredient.

Various modifications of the compounds and processes of the invention may be prepared without departing from the spirit or scope thereof and it is to be understood that the invention is intended to be limited only as defined in the appended claims.

What we claim is:

1. A compound of the formula

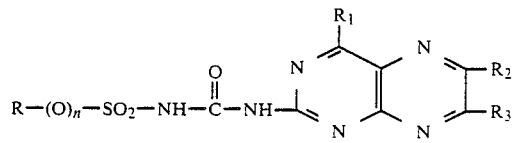

wherein
R is 2,2,2-trichloroethyl or

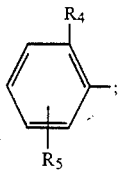

$R_1$ is methoxy, amino, mono(alkyl of 1 to 2 carbon atoms)-amino or di(alkyl of 1 to 2 carbon atoms)-amino;

$R_2$ and $R_3$ are each independently hydrogen or methyl;

$R_4$ is halogen, methoxy, trifluoromethyl, lower alkoxy-carbonyl or dimethylcarbamoyl;

$R_5$ is hydrogen, lower alkyl, lower alkoxy or halogen; and n is 0 or 1;

or a salt thereof.

2. A compound of claim 1,
where
R is 2,2,2-trichloroethyl;
$R_1$ is methoxy, amino, mono(alkyl of 1 to 2 carbon atoms)-amino or di(alkyl of 1 to 2 carbon atoms)-amino;
$R_2$ and $R_3$ are each independently hydrogen or methyl;
$R_4$ is halogen, methoxy, trifluoromethyl, lower alkoxy-carbonyl or dimethylcarbamoyl;
$R_5$ is hydrogen, lower alkyl, lower alkoxy or halogen; and
n is 1.

3. A compound of claim 1, which is N-(4-methoxypteridin-2-yl)-N'-(2-chlorophenylsulfonyl)-urea, N-(4-dimethylamino-6,7-dimethylpteridin-2-yl)-N'-(2-carbomethoxyphenylsulfonyl)-urea, N-(4-methoxy-6,7-dimethylpteridin-2-yl)-N'-(2-carbomethoxyphenylsulfonyl)-urea, N-(4-methoxypteridin-2-yl)-N'-(2-fluorophenoxysulfonyl)-urea, N-(4-methoxypteridin-2-yl)-N'-(2-trifluoromethylphenylsulfonyl)-urea, N-(4-dimethylaminopteridin-2-yl)-N'-(2-chlorophenylsulfonyl)-urea, N-(4-dimethylaminopteridin-2-yl)-N'-(2-methoxycarbonylphenylsulfonyl)-urea, N-(4-methoxypteridin-2-yl)-N'-(2-carbomethoxyphenylsulfonyl)-urea or N-(4-methoxypteridin-2-yl)-N'-(2,2,2-trichloroethoxysulfonyl)-urea.

4. An herbicidal composition consisting essentially of an inert carrier and an effective herbicidal amount of a compound of claim 1.

5. An herbicidal composition consisting essentially of an inert carrier and an effective herbicidal amount of a compound of claim 2.

6. An herbicidal composition consisting essentially of an inert carrier and an effective herbicidal amount of a compound of claim 3.

7. The method of combatting weeds, which comprises contacting said weeds with an herbicidally effective amount of a compound of claim 1.

8. The method of combatting weeds, which comprises contacting said weeds with an herbicidally effective amount of a compound of claim 2.

9. The method of combatting weeds, which comprises contacting said weeds with an herbicidally effective amount of a compound of claim 3.

* * * * *